United States Patent [19]

Thies et al.

[11] Patent Number: 4,464,317

[45] Date of Patent: Aug. 7, 1984

[54] METHOD OF ENCAPSULATING ACTIVE AGENTS WITH INORGANIC COATINGS

[75] Inventors: Curt Thies, Ballwin; Francis W. Linek, Affton, both of Mo.

[73] Assignee: The Washington University, St. Louis, Mo.

[21] Appl. No.: 361,387

[22] Filed: Mar. 24, 1982

Related U.S. Application Data

[63] Continuation-in-part of Ser. No. 116,043, Jan. 28, 1980, abandoned.

[51] Int. Cl.$^3$ .................... B01J 13/02; A01N 25/28; A61K 9/26
[52] U.S. Cl. .................... 264/4.3; 71/DIG. 1; 424/19; 424/22; 427/213.32; 427/344
[58] Field of Search .................... 424/19, 22; 427/344, 427/213.32; 71/DIG. 1; 264/4.3; 423/331

[56] References Cited

U.S. PATENT DOCUMENTS

| | | | |
|---|---|---|---|
| 2,243,296 | 5/1941 | Sweetland | 427/344 X |
| 3,301,701 | 1/1967 | Baker et al. | 428/331 |
| 3,785,798 | 1/1974 | Horai et al. | 424/24 X |
| 3,790,497 | 2/1974 | Sato et al. | 264/4.3 |
| 3,854,981 | 12/1974 | Schon et al. | 427/212 |

FOREIGN PATENT DOCUMENTS

762700  12/1956  United Kingdom .................... 264/4

*Primary Examiner*—Richard D. Lovering
*Attorney, Agent, or Firm*—Senniger, Powers, Leavitt and Roedel

[57] ABSTRACT

A method for forming discrete capsules that contain an active agent, such as a pesticide, involves first forming a suspension of the active agent suspended in a solution of an alkali metal silicate such as sodium silicate or a suspension of the active agent suspended in a liquid coacervate resulting from the addition of a coacervation agent such as acetone to the alkali metal silicate solution. The suspension, preferably in the form of droplets formed by ejecting the suspension through an orifice (e.g. a needle), is then contacted with an aqueous solution of a salt such as calcium chloride which reacts with the alkali metal silicate to form an insoluble silicate (e.g., calcium silicate) coating for the active agent while hardening the dispersed active agent in a silicate core matrix. Thus, capsules of the active agent are produced with an insoluble silicate coating. The capsules are maintained in the aqueous salt solution for a sufficient period of time to permit a high degree of conversion of soluble silicate to insoluble silicate. The capsules are then isolated and dried thereby providing structurally intact capsules which act as a free-flow powder. The capsules provide controlled release of the active agent over a prolonged period of time. Methods for preparing such capsules within a three hour period have been devices thereby improving substantially the economics of encapsulating active agents with inorganic coatings. Such brief preparation times are achieved through the use of soluble silicates rich in $SiO_2$ and by increasing the temperature of the aqueous solution of the salt such as calcium chloride to effectively expedite the capsule curing process.

18 Claims, No Drawings

METHOD OF ENCAPSULATING ACTIVE AGENTS WITH INORGANIC COATINGS

CROSS-REFERENCE TO RELATED APPLICATION

This application is a continuation-in-part of our application Ser. No. 116,043, filed Jan. 28, 1980, and now abandoned.

BACKGROUND OF THE INVENTION

The present invention relates to the field of encapsulation and, more particularly, to methods for encapsulating active agents with an inorganic coating.

The art of encapsulation has developed various processes and methods for individually coating particulate matter for purposes of controlled release or metering out of an active agent over a prolonged period. However, heretofore, such processes have invariably been based upon the use of organic polymers of nonpolymeric organic materials such as fats and waxes as the coating material. Typical prior art processes are described, for example, in U.S. Pat. Nos. 2,800,457, 2,800,458, 3,041,289, 3,341,466, 3,415,758, 3,429,827, 3,594,327, 3,639,256 and 3,674,704. Such complex organic coating materials may be of unknown metabolic fate and therefore not compatible with the environment for applications such as encapsulation of pesticides and insecticidal agents. It would be useful, therefore, to have available an encapsulation system and technique which provides an inexpensive means of producing capsules which are compatible with the environment and which provide effective activity for a prolonged period.

SUMMARY OF THE INVENTION

Among the several objects of the invention may be noted the provision of a method of encapsulating active agents with an inorganic silicate coating; the provision of such a method which produces capsules which are compatible with the environment; the provision of an encapsulation method which produces capsules substantially devoid of organic components; the provision of such a method which can be utilized to encapsulate various types of active agents; the provision of an encapsulation method which may be conveniently and economically carried out; and the provision of an encapsulation method which can be carried out in a relatively short period of time (e.g., 3 hours). Other objects and features will be in part apparent and in part pointed out hereinafter.

The present invention is thus directed to the method of encapsulating an active agent such as a pesticide with an inorganic coating. The method comprises the steps of forming (a) a suspension containing the active agent suspended in a solution of an alkali metal silicate or (b) a suspension containing the active agent suspended in a liquid coacervate resulting from the addition of a coacervation agent to a solution of an alkali metal silicate, contacting the suspension with an aqueous solution of a salt which reacts with an alkali metal silicate to form an insoluble silicate coating for said active agent whereby capsules of the active agent with an insoluble silicate coating are formed, maintaining the capsules in the aqueous salt solution for a time sufficient to harden the silicate capsules, isolating the capsules and thereafter drying the capsules.

The invention is further directed to the method of encapsulating an active agent with an inorganic coating which comprises the steps of:

forming (a) a suspension containing the active agent suspended in a solution of an alkali metal silicate rich in $SiO_2$ or (b) a suspension containing the active agent suspended in a liquid coacervate resulting from the addition of a coacervation agent to a solution of an alkali metal silicate rich in $SiO_2$; contacting the suspension with an aqueous solution of a salt which reacts with an alkali metal silicate to form an insoluble silicate coating for said active agent whereby capsules of the active agent with an insoluble silicate coating are formed, said aqueous solution of a salt which reacts with an alkali metal silicate being maintained at a temperature in the range of approximately 50° C.–85° C. to expedite the curing or hardening of said capsules; maintaining said capsules in said aqueous salt solution for a time sufficient to harden the silicate capsules, isolating the capsules; and thereafter drying the capsules, whereby capsules may be prepared within a total period of approximately 3 hours.

DESCRIPTION OF THE PREFERRED EMBODIMENTS

In accordance with the present invention, we have now found that capsules or pellets of active agents having an inorganic coating may be economically and conveniently prepared by first suspending the active agent or internal phase in a solution of an alkali metal silicate or in a liquid coacervate of an alkali metal silicate solution, contacting the suspension, preferably in droplet form, with an aqueous solution of a salt which reacts with an alkali metal silicate to form an insoluble silicate coating for the active agent, maintaining the capsules thus formed in the aqueous salt solution for a time sufficient to harden the silicate capsules and thereafter isolating and drying the capsules. Also, as noted hereinafter, it has further been found that by appropriate adjustment of the key process parameters of the invention, satisfactory capsules may be prepared in a relatively short period of time, i.e., approximately 3 hours. Through the present invention, capsules are produced which permit the lifetime of the active agent to be extended and the agent to be metered out over a prolonged period, i.e., permit controlled release of the active agent.

Insoluble silicate coating capsules provide several important advantages over controlled release devices based on organic polymer coating materials or nonpolymeric organic coating materials such as fats and waxes. Thus, the alkali metal silicate compounds used in the present invention are plentiful and relatively inexpensive. Further, silicates are strong ultraviolet absorbers so that chemical active agents sensitive to sunlight receive a high degree of protection when encapsulated according to the method of the invention and have enhanced light stability under field conditions. Accordingly, no organic light absorbers need to be added to the capsules produced by the present invention. Finally, silicate capsules are compatible with the environment since they contain essentially nothing other than the active agent and the silicate. Once they release their active payload, such capsules simply function as grains of sand. Capsules of this type may thus be incorporated in or on top of soil and advantageously do not contain complex organic or inorganic compounds of unknown metabolic fate.

Capsules produced in accordance with the present invention may have the traditional capsule structure wherein a core (liquid or solid) is surrounded or engulfed by a silicate coating or may have an outer insoluble silicate shell with the interior being essentially a dispersion of active agent particles or droplets in a silicate matrix.

The method of the present invention is applicable to the encapsulation of a broad spectrum of active agents. Thus, the active agent may be one of the many solid or liquid pesticides used for agricultural purposes or one of the many insecticidal agents which function to poison insects, affect insect growth or interfere with the insect's ability to mate. Other active agents suitable for encapsulation include herbicidal agents, fungicides, mildew preventative agents and algaecides used to control algae formation in aqueous process streams and other industrial environments. The active agent may also be an agent used to control pests which affect human health such as mosquito control agents, snail control agents, fly control agents and the like. The encapsulation method may also be applied to drug materials, insect pheremones, and various agents which affect plant growth and development. These agents could include trace mineral elements (e.g., selenium, boron, etc.) as well as organic compounds known to affect plant growth (e.g., $\alpha$-naphthaleneacetic acid and indole-3-acetic acid).

In the practice of the present invention, the first step involves the formation or preparation of a suspension containing the active agent. The suspension may be simply a suspension of the active agent in a solution of an alkali metal silicate. Preferably, the suspension is one in which the active agent is suspended in a liquid coacervate resulting from the addition of a coacervation agent to a solution of an alkali metal silicate. Through the use of such a liquid coacervate, it has been possible to produce capsules which are more uniform in shape and which exhibit less of a tendency to crumble when handled in the dry state. Preferably, and particularly for the purpose of preparing capsules within a relatively short period of time, commercially available soluble sodium silicates rich in $SiO_2$ are employed in the practice of the invention. The commercially available soluble sodium silicates differ in the weight ratio of $SiO_2/Na_2O$ as well as density, pH and viscosity. Thus, commercial soluble sodium silicates having $SiO_2/Na_2O$ ratios of approximately 1.60 to approximately 3.75 by weight may be utilized, it being understood that the higher the $SiO_2/Na_2O$ ratio, the more readily insolubilized the soluble silicate becomes within the scope of the present invention. To achieve rapid silicate capsule cure on the order of approximately 3 hours as opposed to longer period on the order of two to four weeks, a solution of sodium silicate having an $SiO_2/Na_2O$ ratio (by weight) of 3.75 is employed. Such a product is that marketed under the trade designation "S-35" by the PQ Corporation. Other soluble silicates similarly rich in $SiO_2$ may also be used. Among other sodium silicates which may be employed are those marketed under the trade designations "Stixso-RR" (having an $SiO_2/Na_2O$ ratio of 3.25 (by weight) and "RU" (having an $SiO_2/Na_2O$ ratio of 2.40 (by weight)) by The PQ Corporation. While the use of a sodium silicate solution is preferred, it will be understood that other soluble alkali metal silicates such as potassium, lithium, cesium and rubidium silicates may also be employed in the practice of the invention. In addition to alkali metal silicates quarternary ammonium silicates may be employed.

As stated, the initial suspension is preferably formed by suspending the active agent in a liquid coacervate resulting from the addition of a coacervation agent to the alkali metal silicate solution. The active agent(s) must be well dispersed in said coacervate. Soluble silicate solutions form liquidus coacervates in the presence of certain coacervation agents. Among the coacervation agents which may be used may be mentioned water miscible nonpolymeric solvents such as acetone, ethyl alcohol, ethyl cellasolve, para-dioxane, tetrahydrofuran and dimethylformamide. Aqueous salt ions can also be used. The addition of the coacervation agent to the alkali metal silicate solution yields a two-phase system: a liquid coacervate and a supernatant phase. The active agent is suspended in the liquid coacervate phase. Formation of the coacervate does not involve the use of any organic polymer. The viscosity of the silicate/active agent suspension or mixture is of some significance in that there should be sufficient viscosity to keep the active agent dispersed and yet not too high a viscosity that manufacturing problems arise. Silicate/active agent mixtures which are too low in viscosity do not form regular-shaped particles or capsules but tend to form long-tailed particles. In general, particularly for capsules formed by droplet expulsion of the suspension as described hereinafter, the viscosity of the suspension should range between approximately 20 and 620 centipoises as measured at 30° C. in a Ubellohde viscometer. The preferred viscosity range is between approximately 40 and 300 centipoises.

Once the initial suspension is prepared as described, it is contacted with an aqueous solution of a salt such as calcium chloride which reacts with an alkali metal silicate to form an insoluble silicate coating and/or matrix for the active agent. In the most preferred embodiment of the invention, this is accomplished by converting the suspension into droplet form as by ejecting it through a needle (e.g. in the 15 to 22 gauge range) into the aqueous salt solution or hardening solution. The size of the ejection orifice affects droplet size and hence, the size of the capsules produced, i.e., small droplets produce smaller capsules than large drop- lets.

Moreover, we have found that the drop size (soluble silicate plus active agent droplet) affects the rate and degree of cure achieved. Smaller droplets cure more rapidly and thoroughly than large ones. Such smaller droplets can be formed by using smaller ejection orifices within the above range and/or a surfactant. The surfactant functions to reduce the size of pendant silicate/active agent droplets produced by the orifice. Various surfactants known to the art, such as that marketed under the trade designation "Atlox 3409F" by ICI, may be used in the practice of the invention.

When the silicate/active agent suspension, preferably in the form of droplets, contacts the aqueous solution of calcium chloride, for example, the calcium chloride reacts with the alkali metal silicate to form insoluble calcium silicate which acts as a capsule coating for the particles of the active agent. Because of its availability and low cost, calcium chloride is the preferred material for use in insolubilizing the soluble silicate to produce capsules. However, it will be understood that aqueous solutions of any salt which reacts with the alkali metal silicate to form an insoluble silicate coating for the active agent may likewise be employed in the practice of the invention. Thus, other alkali earth metal salts such as those of barium, strontium and magnesium, or salts of other metals such as manganese or aluminum may be employed to form insoluble silicate coatings in the production of capsules. The amount of salt (e.g., $CaCl_2$) used is preferably in excess of the stoichiometric amount required.

Depending upon the concentration of the silicate insolubilizing metal salt solution (i.e., hardening solution) in contact with the silicate/active agent suspension, the residence time of the suspension in the salt hardening solution and the temperature of the hardening solution, a variety of capsules with varying properties may be obtained. With regard to the concentration of the hardening solution, it has been found that as the molarity of the hardening solution is increased, the storage or residence time required to produce capsules which break up more slowly decreases. Also, the density of the silicate/active agent suspension is preferably greater than that of the hardening solution so that the embryo capsules initially formed will sink to the bottom of a storage container for further hardening. In general, for the preferred calcium chloride hardening solution, the concentration of the hardening solution may range between approximately 1 and 6.4 molar. The preferred range is between approximately 2.85 and 6.4 molar.

As to the temperature of the hardening solution, it has been found that carrying out the silicate capsule hardening process at elevated temperatures accelerates the hardening or insolubilizing reaction. For example, 2 to 4 weeks of hardening of the silicate/active agent suspension in the hardening or insolubilizing solution at 25° C. may be achieved in 2 to 3 hours at 85° C. If the material being encapsulated is a volatile liquid, one should obviously operate at sufficiently low temperatures to minimize volatilization losses. Also, if the active agent is a low melting solid, precautions should be taken at elevated temperatures to avoid bleed-out of the molten material from the capsules while the capsules are being hardened. As a broad range, the temperature of the hardening solution may range from the freezing point of the hardening or aqueous salt solution and the boiling point of the solution as will be apparent to those skilled in the art.

In further accordance with the present invention, it has now been found that the temperature of the salt (e.g., $CaCl_2$) bath has a significant effect on increasing or expediting the curing or hardening process. In terms of the insoluble silicate coating, it has been determined by analysis on an electron probe microscope that increasing the temperature of the curing bath increases the thickness of the insoluble silicate coating. This coating can be as thick as 100 μm for the examples quoted herein. Thus, using a soluble silicate rich in $SiO_2$ as aforesaid, we have found that maintaining the aqueous solution of the salt which reacts with the alkali metal silicate at a temperature in the preferred range of approximately 50° C.–85° C. results in a substantially shortened capsule curing or hardening period. For example, a hardening solution temperature of 85° C. for a period of two hours provides a high degree of insolubilization, a temperature of 70° C. for two hours provides an intermediate degree of insolubilization while a temperature of 55° C. for two hours gives a low degree of cure within this range. Moreover, by varying the temperature of the curing or hardening solution, it is possible to prepare capsules with varying differences in their rate of break-up. For example, capsules formed at a curing temperature of 85° C. break up the slowest while those formed at a curing temperature of 55° C. break up more rapidly.

The residence time of the silicate/active agent suspension in the hardening or aqueous salt solution may also influence the quality of the capsules produced and the properties of the capsules. It has been experimentally determined that the $SiO_2/M_2O$ ratio increases with the residence time in the hardening solution. The higher ratios of $SiO_2/M_2O$ are a measure of the insolubility of the capsules. If it is desired to produce capsules which break up in water at faster rates, shorter residence times, lower hardening solution concentrations and/or lower hardening solution temperatures are employed. Conversely, longer residence or storage times, higher hardening solution concentrations and/or higher hardening solution temperatures yield capsules which break up more slowly in water. It has been found that increased temperatures in the hardening or insolubilizing solution are a particularly effective way of preparing capsules which break up more slowly in water. For example, for sparsely water-soluble pesticides, capsules which fragment rapidly into small pieces upon immersion in water are desirable and we have found that such capsules show 40 to 70% break up after 2 to 7 days storage in stagnant water.

As a specific matter, short residence or storage times in the hardening solution, low concentrations of the aqueous insolubilizing salt in the hardening solution and/or low aqueous salt/silicate mass ratios give capsules with an outer shell that is water-insoluble silicate while the interior is still largely water-soluble alkali metal silicate. When such capsules are dried and resuspended in fresh water, they rapidly disintegrate. Fragments of the insoluble outer shell remain, but any soluble silicate remaining dissolves in water. Therefore, the presence of the soluble alkali metal silicate in the interior of the capsule causes much of the capsule coating material to simply disappear upon immersion in water thereby causing accelerated release of the active agent.

On the other hand, if the capsules initially formed upon contact of the silicate/active agent suspension with the hardening or insolubilizing solution are kept in the hardening solution for the prolonged periods previously mentioned, the conversion of the soluble silicate to insoluble silicate progresses to a high degree of completion. In such cases, the silicate present in the capsules is exceedingly less soluble than the original silicate or silicate coacervate used.

During the period of maintenance of the silicate/active agent suspension in contact with the hardening solution, it is desirable to periodically agitate the capsules gently thereby assuring uniform $CaCl_2$ concentration in the solution. This also minimizes capsule agglomeration.

Once the capsules have been formed and have hardened as described, the capsules are isolated by separation from the hardening or aqueous salt solution. The capsules must then be subjected to drying before use. The time and temperature for the drying step may vary widely. There is no real maximum drying time, but the shortest drying time is limited by the time needed to achieve structurally intact capsules which function as free-flow granules or powders. The drying temperature has importance for two reasons. First, too high a drying temperature may cause volatilization, thermal degradation or bleed-out from the capsule of the active agent. Secondly, high drying temperatures above 50° C. or so tend to yield silicate capsules that do not break up in water. Such capsules tend to float also because the heat-dried capsules are want to expand on drying thereby forming a porous sponge-like mass which can float due to entrapped air pockets. Of course, for applications in which floating silicate capsules are desired, drying at elevated temperatures can be used to obtain such capsules. In broad terms, therefore, the time of drying may range from minutes to a month at any temperature and/or relative humidity condition unharmful to the active agent. Preferably, the drying temperature ranges between approximately 20° and 50° C. for a period between 1-3 hours and approximately 2 weeks. Drying at temperatures below 50° C. is definitely preferred where longer curing times are used and it is not desired to produce capsules in a short period.

However, where it is desired to produce capsules of acceptable quality in a relatively short time period (e.g., 3 hours), a drying temperature of 80° C. to 120° C. is preferred.

The capsules produced in accordance with the present invention are characterized by having the pesticide or other active agent substantially uniformly dispersed throughout, i.e., a silicate matrix/membrane/coating surrounds a silicate matrix core throughout which the active agent is dispersed.

Actual field tests have shown that capsules prepared in accordance with the method of the present invention are capable of fragmenting upon storage in water to provide controlled release of a mosquito control agent. In fact, these field tests show that the lifetime of the mosquito control agent (active agent) was at least doubled when encapsulated according to the present invention as compared to the performance of the unencapsulated material.

The following examples illustrate the practice of the invention.

EXAMPLE 1

Cyclazocine, a narcotic antagonist, was suspended in a soluble sodium silicate solution (marketed under the trade designation "RU" by Philadelphia Quartz Co.). The suspension was then dropped at room temperature into an aqueous calcium chloride solution (1 M). Large pellets (3000–4000μ) were obtained. These pellets were subjected to a rotating bottle extraction procedure at a pH of 7.4 and a temperature of 37° C. with the following results:

| Test pellet | Extraction Time (hr.) | Mg Cyclazocine Extracted |
|---|---|---|
| #1 (57 mg) | 2.0 | 6.41 |
| | 75.0 | 8.44 |
| #2 (120 mg) | 2.0 | 7.05 |
| | 125.0 | 10.95 |
| #3 (55 mg) | 1.0 | 2.59 |
| | 48.0 | 7.76 |
| | 72.0 | 8.40 |

Thus, the pellets or capsules are releasing cyclazocine over a prolonged time period. The cyclazocine constituted approximately 10 to 15% of the pellet's total weight.

EXAMPLE 2

Water (160 ml) was added to a sodium silicate solution (400 ml "RU" brand) and the two were thoroughly mixed together. Acetone (40 ml) was then added to yield a two-phase liquid. The liquid was thoroughly mixed and then allowed to settle undisturbed for three hours. The coacervate which had formed was collected and a pesticide (20 g of 75 wt % wettable powder sold under the trade designation "Furadan" by FMC Corporation) was added and thoroughly stirred in. The resulting suspension was ejected through both 21 and 15 gauge needles into a calcium chloride solution (2.85 M). The capsules which formed were allowed to remain in the calcium chloride solution for 12 days. The capsules were then isolated, rinsed with water and air dried for two weeks. The entire procedure was performed at a mean temperature of 24° C.

EXAMPLE 3

Water (40 ml) was added to a sodium silicate solution (400 ml "RU" brand) and the two thoroughly mixed together. A pesticide (20 g of 75 wt % wettable powder "Furadan" by FMC Corporation) was added and thoroughly stirred in. The resulting suspension was ejected through both 21 and 15 gauge needles into a calcium chloride solution (2.85 M). The capsules which formed were allowed to remain in the calcium chloride solution for 12 days and then isolated, rinsed with water and air dried for two weeks. The entire procedure was performed at a mean temperature of 24° C.

EXAMPLE 4

Water (20 ml) was added to a sodium silicate solution (50 ml "RU" brand) and the two thoroughly mixed together. Acetone (5 ml) was then added to yield a two-phase liquid. The liquid was thoroughly mixed and then allowed to settle undisturbed for three hours. The coacervate which had formed was collected and a pesticide (1.48 g of 2-(2,4,5-trichloro-phenoxy)-propionic acid, Aldrich Chemical Co.) was added and thoroughly stirred in. The resulting suspension was ejected through an 18 gauge needle into a calcium chloride solution (2.85 M). The capsules which formed were allowed to remain in the calcium chloride solution for 20 days and then isolated, rinsed with water and air dried for two weeks. The entire procedure was performed at a mean temperature of 24° C.

EXAMPLE 5

Water (10 ml) was added to a sodium silicate solution (50 ml, "RU" brand) and the two thoroughly mixed together. A pesticide (2.32 g of 2-(2,4,5-trichlorophenoxy)-propionic acid, Aldrich Chemical Co.) was added and thoroughly stirred in. The resulting suspension was ejected through an 18 gauge needle into a calcium chloride solution (2.85 M). The capsules which formed were allowed to remain in the calcium chloride solution for 20 days and then isolated, rinsed with water and air dried for two weeks. The entire procedure was performed at a mean temperature of 24° C.

EXAMPLE 6

Water (250 ml) was added to a sodium silicate solution (50 ml, "RU" brand) and the two thoroughly mixed together. Acetone (100 ml) was then added to yield a two-phase liquid. The liquid was thoroughly mixed and allowed to settle undisturbed for three hours. At this time the coacervate was collected and a pesticide (1.30 g of 2-(2,4,5-trichloro-phenoxy)-propionic acid by Aldrich Chemical Co.) was added and thoroughly stirred in. The resulting suspension was ejected through an 18 gauge needle into a calcium chloride solution (2.85 M). The capsules were allowed to remain in the calcium chloride solution for 20 days and were then isolated, rinsed with water and air dried for two weeks. The entire procedure was performed at a mean temperature of 24° C. These capsules were able to prevent root development of "Grand Rapids lettuce seeds" under laboratory conditions for 22–24 weeks.

EXAMPLE 7

Example 5 was repeated except that 1.98 g of the pesticide 2,4-dichlorophenoxy acetic acid (Aldrich Chemical Co.) and a 15 gauge needle were employed.

EXAMPLE 8

Example 4 was repeated except that 1.66 g of the pesticide 2,4-dichlorophenoxy acetic acid (Aldrich Chemical Co.) and a 15 gauge needle were employed.

EXAMPLE 9

Example 6 was repeated except that 1.23 g of the pesticide 2,4-dichlorophenoxy acetic acid (Aldrich Chemical Co.) and a 15 gauge needle were employed.

EXAMPLE 10

Example 6 was repeated except that 37.50 ml of water, 750 ml of the sodium silicate solution and 1500 ml of acetone were used and 31.14 g of the pesticide "Altosid" (40 wt % in carbon black; Zoecon Corp.) and a 15 gauge needle were employed.

EXAMPLE 11

Example 6 was repeated except that 394 ml of water, 972 ml of the sodium silicate solution and 99 ml of acetone were used and 44.9 g of the pesticide "Altosid" (40 wt % in carbon black; Zoecon Corp.) and a 15 gauge needle were employed. Also, the calcium chloride solution had a molarity of 3.6.

EXAMPLE 12

Example 5 was repeated except that 211 ml of water and 967 ml of the sodium silicate solution were used and 45.01 g of the pesticide "Altosid" (40 wt % in carbon black; Zoecon Corp.) and a 15 gauge needle were employed.

EXAMPLE 13

Water (30 ml) was added to a sodium silicate solution (150 ml "RU" brand) and the two thoroughly mixed together. A pesticide (10 g of "Thiofanox", Diamond Shamrock) dissolved in acetone (18 ml) was added and thoroughly stirred in. The resulting suspension was ejected through 15 gauge needles into a calcium chloride solution (2.85 M). The capsules were allowed to remain in the calcium chloride solution for 25 days and were then isolated, rinsed with water and air dried for two weeks. The entire procedure was performed at a mean temperature of 24° C.

EXAMPLE 14

Water (3750 ml) was added to a sodium silicate solution (750 ml, "RU" brand) and the two thoroughly mixed together. Acetone (1500 ml) was then added to yield a two-phase liquid. The liquid was thoroughly mixed and allowed to settle undisturbed for 3 hours. At this time the coacervate was collected and a pesticide (30 ml of liquid Abate, American Cyanamid, Stamford, Conn.) (Formula E-4, 43% actives formulated by Thompson Hayward Co., Kansas City, Kans.) was added and thoroughly stirred in. The resulting suspension was ejected through 15 gauge needles into a calcium chloride solution (4.1 M). At the end of the ejections, the flask containing the capsules in calcium chloride was sealed and placed in a 60° C. water bath for 4 days and the capsules were then isolated, rinsed with water, and air dried for 2 weeks. The entire procedure, except for the calcium chloride reaction time, was performed at a mean temperature of 24° C. Example 14 was repeated except that the capsules were stored for 21 days at 25° C. The capsules were tested. The results indicated 150 days of control in the laboratory and 75 days of control in field tests in rice patties in Arkansas.

EXAMPLE 15

Water (2500 ml) was added to a sodium silicate solution (500 ml "RU" brand) and the two thoroughly mixed together. Acetone (1000 ml) was then added to yield a two-phase liquid. The liquid was thoroughly mixed and allowed to settle undisturbed for 3 hours. At this time the coacervate was collected and a pesticide (16.9 g Dimilin®, Technical, A.I. 99%, Thompson-Hayward Chemical Co., Kansas City, Kans.) was added and throughly stirred in. The resulting suspension was ejected through 15 gauge needles into a calcium chloride solution (3 M). The capsules were allowed to remain in the calcium chloride solution for 3 weeks and were then isolated, rinsed with water and air dried for 2 weeks. The entire procedure was performed at a mean temperature of 24° C.

EXAMPLE 16

Water (450 ml) was added to a sodium silicate solution (90 ml "RU" brand) and the two thoroughly mixed together. Acetone (180 ml) was then added to yield a two-phase liquid. The liquid was thoroughly mixed and allowed to settle undisturbed for 3 hours. At this time, the coacervate was collected and a pesticide (7.46 g of Dursban®, Dow Chemical Co., Midland, Mich.) was added and thoroughly stirred in. The resulting suspension was ejected through 18 gauge needles into a calcium chloride solution (3 M). The capsules were allowed to remain in the calcium chloride solution for 1 week and were then isolated, rinsed with water and air dried for 2 weeks. The entire procedure was performed at a mean temperature of 24° C.

EXAMPLE 17

A pesticide (0.6766 g of "Abate E-4", an emulsifiable concentrate of "Abate", American Cyanamid, Stamford, Conn.) was thoroughly emulsified into sodium silicate (13.4375 g of "S-35" sodium silicate having a $SiO_2/Na_2O$ ratio of 3.75 (by weight), The PQ Corporation, Valley Forge, Pa.). A calcium chloride solution (80 ml of 3.8 M solution) was placed in a 55° C. water bath. After allowing 10 minutes for the calcium chloride solution to equilibrate to 55° C., the above prepared pesticide/sodium silicate emulsion or suspension (12.419 g) was dropwise extruded through an 18 gauge needle into the calcium chloride solution. The capsules which formed sank very slowly. The capsules were isolated after 2 hours, rinsed, and towel dried. At this time, the capsules weighed 5.9584 g. After oven drying for one hour at 100° C., the capsules weighed 5.1946 g.

EXAMPLE 18

A pesticide (0.8005 g of "Abate E-4") was thoroughly emulsified into sodium silicate (13.6507 g of "S-35"). A calcium chloride solution (80 ml of 2.8 M solution) was placed into a 70° C. water bath. After allowing 10 minutes for the calcium chloride solution to equilibrate to 70° C., the above-prepared pesticide/sodium silicate emulsion or suspension (12.3146 g) was extruded dropwise into the calcium chloride solution through an 18 gauge needle. The capsules which formed were isolated after 2 hours, rinsed and blotted dry. At this time, the capsules weighed 5.8793 g. The sample thus prepared was then divided into two batches and dried at different conditions. Sample A (5.1706 g) was dried for 1 hour at 100° C. and then weighed 4.4477 g. Sample B (0.7049 g) was dried for ½ hour at 100° C. at which time the oven was turned up to 120° C. for another ½ hour. The sample weighed 0.6004 g after the final drying at 120° C.

EXAMPLE 19

A pesticide (0.7547 g of "Abate E-4") was thoroughly emulsified into sodium silicate (13.0018 g of "S-35"). This emulsion or suspension (11.4165 g) was then extruded through an 18 gauge needle into a 3.5 M calcium chloride solution equilibrated to 85° C. in a water bath. The capsules which formed were isolated after 2 hours and found to weigh 5.1359 g. The capsules were then transferred to an oven and dried for ½ hour at 100° C., followed by ½ hour at 120° C. The sample weighed 4.553 g after the final drying at 120° C.

EXAMPLE 20

Capsules were prepared by emulsifying 10 drops of dioctyl phthalate (SC 11946, Sargent Welch Scientific), 1 drop of a surfactant ("Atlox 3409F", ICI and a pinch of Oil Red O No. 0625 (Sigma-Aldrich Chemical Company) into 2.5 ml of a sodium silicate solution ("S-35"). This suspension was extruded through an 18 gauge needle into a 2.8 M calcium chloride solution equilibrated to 70° C. After 2 hours, the capsules which formed were isolated and dried at 110° C. for 1 hour.

EXAMPLE 21

Example 20 was repeated using sodium silicate marketed under the trade designation "Stixso-RR" (a grade of soluble sodium silicate having an $SiO_2/Na_2O$ ratio of 3.25 (by weight), The PQ Corporation) instead of "S-35" and a 4 M calcium chloride solution instead of a 2.8 M calcium chloride solution. Technical "Abate" (10 drops), "Atlox 3409F" (3 drops) and a pinch of Oil Red O No. 0625 were emulsified into 5 ml of the sodium silicate solution ("Stixso-RR"). The suspension was extruded into a 4 M calcium chloride solution equilibrated to 70° C. through an 18 gauge needle. After 2 hours, the capsules which formed were isolated and dried for 1 hour at 110° C.

EXAMPLE 22

Example 21 was repeated using a 15 gauge needle. Satisfactory capsules were obtained.

EXAMPLE 23

Example 21 was repeated using a drying procedure of 20 minutes at 80° C., 20 minutes at 100° C. and 20 minutes at 120° C. Satisfactory capsules were obtained.

EXAMPLE 24

Example 21 was repeated using a drying procedure of 20 minutes at 80° C., 20 minutes at 100° C. and 20 minutes at 120° C. A 15 gauge needle was used to form the capsules by ejection.

In view of the above, it will be seen that the several objects of the invention are achieved and other advantageous results attained.

As various changes could be made in the above methods and products without departing from the scope of the invention, it is intended that all matter contained in the above description shall be interpreted as illustrative and not in a limiting sense.

What is claimed is:

1. The method of encapsulating an active agent with an inorganic coating which comprises the steps of:
    forming (a) a suspension containing the active agent suspended in a solution of an alkali metal silicate having an $SiO_2$ to alkali metal oxide ($M_2O$) ratio between approximately 1.60 and 3.75 by weight or (b) a suspension containing the active agent suspended in a liquid coacervate resulting from the addition of a coacervation agent to a solution of an alkali metal silicate having an $SiO_2$ to alkali metal oxide ($M_2O$) ratio between approximately 1.60 and 3.75 by weight;
    contacting the suspension with an aqueous solution of a salt which reacts with said alkali metal silicate to form an insoluble silicate coating for said active agent whereby capsules of the active agent with an insoluble silicate coating are formed, said insoluble silicate coating having a thickness of up to 100 $\mu$m and said aqueous solution of a salt which reacts with said alkali metal silicate being maintained at a temperature in the range of approximately 50° C.–85° C. to expedite the curing or hardening of said capsules;
    maintaining said capsules in said aqueous salt solution for a time sufficient to harden the silicate capsules; and
    isolating the capsules;
    thereafter drying the capsules,
    said capsules being characterized by having the active agent substantially uniformly dispersed throughout.

2. The method as set forth in claim 1 wherein the aklali metal silicate is sodium silicate having an $SiO_2/Na_2O$ ratio of 3.75 by weight.

3. The method as set forth in claim 1 wherein the aqueous solution of a salt which reacts with an alkali metal silicate to form an insoluble silicate coating is an aqueous solution of a salt of an alkaline earth metal.

4. The method as set forth in claim 3 wherein the aqueous solution of a salt which reacts with an alkali metal silicate to form an insoluble silicate coating is an aqueous solution of calcium chloride.

5. The method as set forth in claim 4 wherein the temperature of said aqueous solution is maintained at approximately 85° C.

6. The method as set forth in claim 4 wherein the molarity of the calcium chloride solution ranges from approximately 1 to 6.4.

7. The method as set forth in claim 1 wherein the active agent is selected from the group consisting of pesticides, insecticidal agents, fungicides, herbicides, algaecides, mildew preventative agents, drugs, mosquito control agents and plant growth agents.

8. The method as set forth in claim 1 wherein the coacervation agent is a water miscible nonpolymeric solvent.

9. The method as set forth in claim 1 wherein the capsules are dried at a temperature in the range of approximately 80° C.–120° C.

10. The method as set forth in claim 9 wherein the capsules are dried at a temperature of approximately 120° C.

11. The method of encapsulating an active agent with an inorganic coating which comprises the steps of:

forming a suspension containing the active agent suspended in a liquid coacervate resulting from the addition of a coacervation agent to a solution of an alkali metal silicate having an $SiO_2$ to alkali metal exide ($M_2O$) ratio between approximately 1.60 and 3.75 by weight, said suspension having a viscosity of between approximately 20 and 620 centipoises as measured at 30° C. in a Ubbelohde viscometer;

contacting the suspension with an aqueous solution of a salt which reacts with an alkali metal silicate to form an insoluble silicate coating for said active agent whereby capsules of the active agent with an insoluble silicate coating are formed said insoluble silicate coating having a thickness of up to 100 μm and said aqueous solution of a salt which reacts with said alkali metal silicate being maintained at a temperature in the range of approximately 50°–85° C. to expedite the curing of hardening of said capsules;

isolating the capsules; and thereafter drying the capsules, said capsules being characterized by having the active agent substantially uniformly dispersed throughout.

12. The method as set forth in claim 11 wherein the alkali metal silicate is sodium silicate.

13. The method as set forth in claim 11 wherein the aqueous solution of a salt which reacts with an alkali metal silicate to form an insoluble silicate coating is an aqueous solution of a salt of an alkaline earth metal.

14. The method as set forth in claim 13 wherein the aqueous solution of a salt which reacts with an alkali metal silicate to form an insoluble silicate coating is an aqueous solution of calcium chloride.

15. The method as set forth in claim 14 wherein the molarity of the calcium chloride solution ranges from approximately 2.85 to 6.4.

16. The method as set forth in claim 11 wherein said suspension is converted into droplet form prior to contacting said aqueous salt solution.

17. The method as set forth in claim 11 wherein the coacervation agent is a water miscible nonpolymeric solvent.

18. The method as set forth in claim 11 wherein the active agent is selected from the group consisting of pesticides, insecticidal agents, fungicides, herbicides, algaecides, mildew preventative agents, drugs, mosquito control agents and plant growth agents.

* * * * *